(12) United States Patent
Bodas et al.

(10) Patent No.: US 12,240,793 B2
(45) Date of Patent: Mar. 4, 2025

(54) $C_4$ FEEDSTOCK PREPROCESSING FOR MTBE UNITS AND CRACKERS

(71) Applicant: SABIC GLOBAL TECHNOLOGIES B.V., Bergen Op Zoom (NL)

(72) Inventors: Vijay Dinkar Bodas, Riyadh (SA); Mohammed Bismillah Ansari, Riyadh (SA)

(73) Assignee: SABIC Global Technologies B.V., Bergen op Zoom (NL)

( * ) Notice: Subject to any disclaimer, the term of this patent is extended or adjusted under 35 U.S.C. 154(b) by 0 days.

(21) Appl. No.: 18/005,589

(22) PCT Filed: Jul. 16, 2021

(86) PCT No.: PCT/IB2021/056469
§ 371 (c)(1),
(2) Date: Jan. 13, 2023

(87) PCT Pub. No.: WO2022/013840
PCT Pub. Date: Jan. 20, 2022

(65) Prior Publication Data
US 2023/0278940 A1    Sep. 7, 2023

(30) Foreign Application Priority Data
Jul. 17, 2020    (EP) ...................................... 20186356

(51) Int. Cl.
*C07C 2/76*    (2006.01)
*C07C 4/04*    (2006.01)
(Continued)

(52) U.S. Cl.
CPC .................. *C07C 2/76* (2013.01); *C07C 4/04* (2013.01); *C07C 5/2724* (2013.01);
(Continued)

(58) Field of Classification Search
CPC .. C07C 2/76; C07C 4/04; C07C 41/06; C07C 5/27; C07C 5/333; C07C 5/42
See application file for complete search history.

(56) References Cited

U.S. PATENT DOCUMENTS 4,393,250 A * 7/1983 Gottlieb .................. C07C 29/04
568/918
6,020,534 A * 2/2000 Choudhary ............... C07C 5/48
585/650

(Continued)

FOREIGN PATENT DOCUMENTS

CN    103739432    4/2014
CN    104892341    9/2015
(Continued)

OTHER PUBLICATIONS

Extended European Search Report issued in corresponding European Application No. 20186356.0, dated Jan. 12, 2021.
(Continued)

*Primary Examiner* — Sharon Pregler
(74) *Attorney, Agent, or Firm* — Norton Rose Fulbright US LLP

(57) ABSTRACT

Systems and methods for processing a $C_3$ and $C_4$ hydrocarbon mixture have been disclosed. The $C_3$ and $C_4$ hydrocarbon mixture is separated to remove propane from $C_4$ hydrocarbons. The resulting $C_4$ hydrocarbons are then processed in an isomerization unit to produce additional isobutane. The isobutane of the isomerization unit effluent is dehydrogenated in a dehydrogenation unit to produce isobutene. The resulting isobutene is reacted with an alkanol to produce an alkyl tert-butyl ether.

20 Claims, 4 Drawing Sheets

(51) Int. Cl.
      *C07C 5/27*           (2006.01)
      *C07C 5/333*      (2006.01)
      *C07C 5/42*           (2006.01)
      *C07C 41/06*      (2006.01)

(52) U.S. Cl.
      CPC .............. *C07C 5/3337* (2013.01); *C07C 5/42* (2013.01); *C07C 41/06* (2013.01); *C07C 2521/04* (2013.01); *C07C 2523/24* (2013.01); *C07C 2523/42* (2013.01); *C07C 2527/053* (2013.01); *C07C 2527/126* (2013.01)

(56) References Cited

U.S. PATENT DOCUMENTS 10,053,440 B2 *   8/2018   Bolz ........................ C07C 5/32
2018/0002300 A1   1/2018   Bolz et al.

FOREIGN PATENT DOCUMENTS

| CN | 105037108 | 11/2015 |
| --- | --- | --- |
| CN | 104250192 | 3/2016 |
| CN | 105949023 | 9/2016 |
| CN | 106045810 | 10/2016 |

OTHER PUBLICATIONS

International Search Report and Written Opinion issued in corresponding International application PCT/IB2021/056469 mailed Oct. 8, 2021.

Qiang, "Selection of c3 cutting scheme from lpg for producing high purity isobutane" *Petroleum Processing and Petrochemicals,* vol. 50, Issue 12, pp. 17-20, Dec. 12, 2019 (Abstract only).

* cited by examiner

C₄ FEEDSTOCK PREPROCESSING FOR MTBE UNITS AND CRACKERS

CROSS REFERENCE TO RELATED APPLICATIONS

This application is a national phase under 35 U.S.C. § 371 of International Application No. PCT/IB2021/056469, filed Jul. 16, 2021, which claims the benefit of priority to European Patent Application No. 20186356.0, filed Jul. 17, 2020, the entire contents of which are hereby incorporated by reference in their entirety.

FIELD OF INVENTION

The present invention generally relates to a process of producing alkyl tert-butyl ether. More specifically, the present invention relates to a process of producing alkyl tert-butyl ether using a $C_3$ and $C_4$ hydrocarbon mixture as feedstock.

BACKGROUND OF THE INVENTION

One of the most common alkyl tert-butyl ethers is methyl tert-butyl ether (MTBE), which is used as an additive in gasoline to enhance the octane number of the gasoline. Since about 1970, MTBE has been synthesized by etherification of isobutylene by reaction with methanol in the presence of an acidic catalyst. Isobutylene used for MTBE synthesis can be obtained from $C_4$ hydrocarbons. Generally, isobutylene and methanol are fed into a fixed bed reactor to produce an MTBE containing effluent. The effluent is then fed to a reaction column to react isobutylene remaining in the effluent with additional methanol to produce more MTBE.

One of the sources for the $C_4$ hydrocarbons used in the MTBE production process can include liquefied petroleum gas, which includes primarily $C_4$ and $C_3$ hydrocarbons. The liquefied petroleum gas is processed in an isomerization unit and then in a dehydrogenation unit to produce isobutylene. The effluent stream from the dehydrogenation unit(s) is then flowed to an MTBE synthesis unit to react with methanol for producing MTBE. However, the reaction efficiency in the isomerization unit(s) and/or dehydrogenation unit(s) is relatively low when liquefied petroleum gas is used as the feedstock, resulting in high production cost for MTBE.

Overall, while systems and methods for producing MTBE from a $C_4$ and $C_3$ hydrocarbon mixture (e.g., liquefied petroleum gas) exist, the need for improvements in this field persists in light of at least the aforementioned drawback for the conventional systems and methods.

BRIEF SUMMARY OF THE INVENTION

A solution to at least the above mentioned problem associated with the systems and methods for producing alkyl tert-butyl ether, such as MTBE, from a $C_4$ and $C_3$ hydrocarbon mixture (e.g., liquefied petroleum gas) has been discovered. The solution resides in a method for processing a hydrocarbon mixture that includes $C_4$ and $C_3$ hydrocarbons. The method includes separating the hydrocarbon mixture to produce a $C_3$ stream and a $C_4$ stream, isomerizing the n-butane of the $C_4$ stream, and dehydrogenating the isobutane in the $C_4$ stream in a dehydrogenation unit to produce isobutene. An effluent from the dehydrogenation unit is further flowed into an etherification unit for producing alkyl tert-butyl ether. The $C_3$ stream can be further processed in a cracker to produce propylene and/or ethylene. This can be beneficial for at least reducing the inert portion in the feed stream flowed into the isomerization unit and/or the dehydrogenation unit, thereby increasing the reaction efficiency for dehydrogenating isobutane. Furthermore, the disclosed method can reduce or eliminate the large amount of propane in the $C_4$ processing steps, resulting in a feed stream with higher concentration of isobutene being flowed into the MTBE synthesis unit, thereby improving reaction efficiency in the etherification unit, and reducing the amount of gas that is recycled back to the dehydrogenation unit. This can ultimately contribute to reduced production cost for alkyl tert-butyl ether. Therefore, the systems and methods of the present invention provide a technical solution to at least some of the problems associated with the conventional systems and methods for alkyl tert-butyl ether production as mentioned above.

Embodiments of the invention include a method of processing a hydrocarbon mixture. The method comprises separating a hydrocarbon mixture comprising propane, n-butane, and/or isobutane to produce (1) a $C_3$ stream comprising primarily propane, and (2) a $C_4$ stream comprising n-butane and/or isobutane. The method includes cracking the propane of the $C_3$ stream under reaction conditions sufficient to produce propylene. The method includes processing at least a portion of the $C_4$ stream under isomerization conditions sufficient to isomerize n-butane of the $C_4$ stream to produce an isomerization unit effluent comprising isobutane.

Embodiments of the invention include a method of processing a hydrocarbon mixture. The method comprises separating a hydrocarbon mixture comprising propane, n-butane, and/or isobutane to produce (1) a $C_3$ stream comprising primarily propane, and (2) a $C_4$ stream comprising n-butane and/or isobutane. The method includes cracking the propane of the $C_3$ stream under reaction conditions sufficient to produce propylene. The method includes processing at least a portion of the $C_4$ stream under isomerization conditions sufficient to isomerize n-butane of the $C_4$ stream to produce an isomerization unit effluent comprising isobutane. The method includes dehydrogenating the isobutane of the isomerization unit effluent in a dehydrogenation unit to produce isobutene in a dehydrogenation unit effluent. The method further includes reacting, in an etherification unit, the isobutene of the dehydrogenation unit effluent with an alkynol in the presence of a catalyst under reaction conditions sufficient to produce alkyl tert-butyl ether in an etherification unit effluent.

Embodiments of the invention include a method of processing hydrocarbon mixtures. The method comprises separating a first hydrocarbon mixture comprising propane, n-butane, and/or isobutane to produce (1) a first $C_3$ stream comprising primarily propane, and (2) a first $C_4$ stream comprising n-butane and/or isobutane. The method includes separating a second hydrocarbon mixture comprising propane, n-butane, and/or isobutane to produce (a) a second $C_3$ stream comprising primarily propane, and (b) a second $C_4$ stream comprising n-butane and/or isobutane. The method includes cracking the propane of the first $C_3$ stream and the second $C_3$ stream under reaction conditions sufficient to produce propylene. The method further includes cracking the n-butane and/or isobutane of the second $C_4$ stream to produce propylene, ethylene and/or benzene. The method includes processing at least a portion of the first $C_4$ stream under isomerization conditions sufficient to isomerize n-butane of the $C_4$ stream to produce an isomerization unit effluent comprising isobutane. The method includes dehydrogenating the isobutane of the isomerization unit effluent in a dehydrogenation unit to produce isobutene in a dehydrogenation unit effluent. The method includes reacting, in an etherification unit, the isobutene of the dehydrogenation unit effluent with an alkynol in the presence of a catalyst under reaction conditions sufficient to produce alkyl tert-butyl ether in an etherification unit effluent.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which:

FIG. 1A shows a schematic diagram of a system for producing MTBE from a propane-and-butanes mixture that processes $C_3$ and $C_4$ separately; FIG. 1B shows a schematic diagram of a system for producing MTBE from a propane-and-butanes mixture that is integrated with a second propane and butanes processing plant; FIG. 1C shows a schematic diagram of a system for producing MTBE from a propane-and-butanes mixture that processes a portion of $C_4$ in a butane cracker.

DETAILED DESCRIPTION OF THE INVENTION

Currently, MTBE can be produced by processing a $C_3$ and $C_4$ hydrocarbon mixture in an isomerization unit and a dehydrogenation unit, sequentially. The effluent from the dehydrogenation unit comprising isobutene is then fed into a MTBE synthesis unit to produce MTBE. However, the $C_3$ hydrocarbons and lighter hydrocarbons (e.g., methane and $C_2$ hydrocarbons) in the hydrocarbon mixture are inert components that dilute the $C_4$ hydrocarbon reactants in each of the reaction units, thereby reducing the reaction efficiency and increasing the energy consumption for producing MTBE. The present invention provides a solution to the problem. The solution is premised on a system and a method for processing hydrocarbons that includes separating $C_3$ and/or $C_1$ to $C_2$ hydrocarbons from the hydrocarbon mixture before it is processed in an isomerization unit and/or a dehydrogenation unit, resulting in higher isobutane concentration in the feed stream and consequently higher reaction efficiency in the feed stream for the dehydrogenation unit, compared to conventional methods. Moreover, the separated $C_3$ and/or $C_1$ to $C_2$ hydrocarbons can be processed in a steam cracking unit for producing light olefins and/or aromatics, thereby increasing the utilization rate and the overall value of the $C_3$ and $C_4$ hydrocarbon mixture. These and other non-limiting aspects of the present invention are discussed in further detail in the following sections.

A. System for Processing $C_3$ and $C_4$ Hydrocarbon Mixture

Figure 1A:
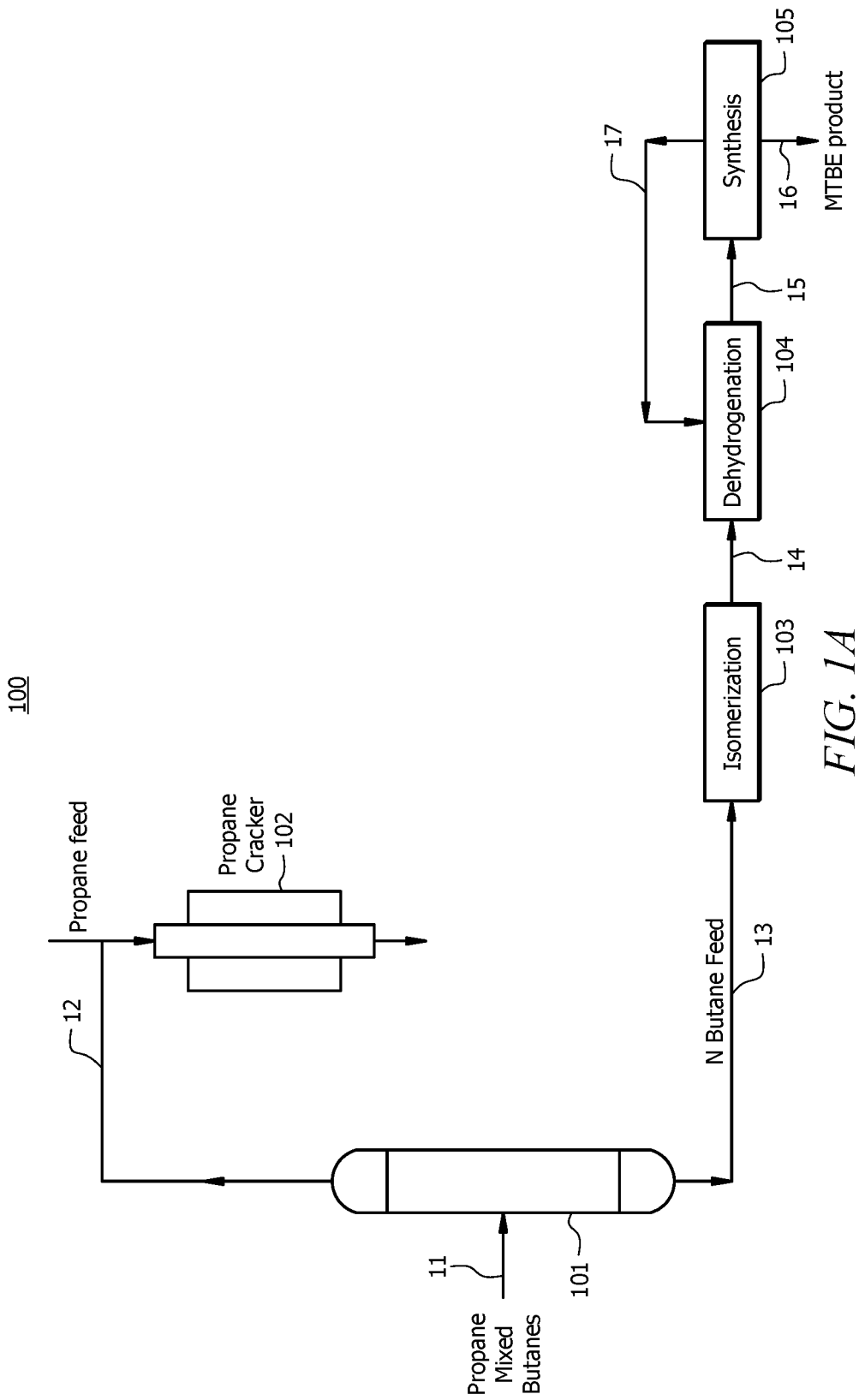
FIGS. 1A-1C show schematic diagrams of systems for producing MTBE, according to embodiments of the invention.

In embodiments of the invention, the system for processing a hydrocarbon mixture comprising $C_3$ and $C_4$ hydrocarbons includes a separation unit, an isomerization unit, a dehydrogenation unit, a steam cracking unit, and an etherification unit. Notably, the system is capable of reducing energy consumption and increasing efficiency for producing an alkyl tert-butyl ether, compared to conventional systems. With reference to FIG. 1A, a schematic diagram is shown for system 100, which is used for producing MTBE using a $C_3$ and $C_4$ mixture as a feedstock.

According to embodiments of the invention, system 100 includes first separation unit 101 configured to separate feed stream 11 comprising $C_3$ hydrocarbons and $C_4$ hydrocarbons to form first $C_3$ stream 12 comprising primarily propane and first $C_4$ stream 13 comprising primarily n-butane and isobutane, collectively. In embodiments of the invention, first separation unit 101 can include a distillation column. The distillation column may include a depropanizer. Feed stream 11, in embodiments of the invention, can include 0 to 7 wt. % propane, 60 to 80 wt. % n-butane, and 20 to 30 wt. % isobutane. In embodiments of the invention, feed stream 11 can include liquefied petroleum gas and may be referred to herein as a first feed stream. In embodiments of the invention, first $C_3$ stream 12 further includes methane and/or $C_2$ hydrocarbons. According to embodiments of the invention, a top outlet of first separation unit 101 is in fluid communication with an inlet of cracking unit 102 such that first $C_3$ stream 12 flows from first separation unit 101 to cracking unit 102. Cracking unit 102 may be configured to crack hydrocarbons of first $C_3$ stream 12 to produce (1) light olefins comprising propylene and/or ethylene, and/or (2) aromatics comprising benzene. In embodiments of the invention, cracking unit 102 includes a propane steam cracker.

According to embodiments of the invention, a bottom outlet of first separation unit 101 is in fluid communication with isomerization unit 103 such that first $C_4$ stream 13 flows from first separation unit 101 to isomerization unit 103. Isomerization unit 103 can be configured to isomerize n-butane of first $C_4$ stream 13 to produce isomerization unit effluent stream 14 comprising isobutane. Isomerization unit 103 can include a fixed bed reactor, a continuous catalytic converter, and/or an adiabatic or a cooled isothermal converter reactor. Isomerization unit 103, in embodiments of the invention, comprises a catalyst including Pt/AlCl$_3$/Al$_2$O$_3$, Pt/AlCl$_3$/zeolite, Pt/SO$_4^{2-}$—ZrO$_2$, SO$_4^{2-}$/ZrO$_2$—Al$_2$O$_3$, or any combination thereof. In embodiments of the invention, additional n-butane can be added into first $C_4$ stream 13.

According to embodiments of the invention, an outlet of isomerization unit 103 is in fluid communication with an inlet of dehydrogenation unit 104 such that isomerization unit effluent stream 14 flows from isomerization unit 103 to dehydrogenation unit 104. In embodiments of the invention, dehydrogenation unit 104 is configured to dehydrogenate isobutane of isomerization unit effluent stream 14 to produce dehydrogenation unit effluent stream 15 comprising isobutene and/or unreacted isobutane. In embodiments of the invention, dehydrogenation unit 104 includes one or more fixed bed reactors, one or more fluidized bed reactors, or one or more continuous catalytic converters. Dehydrogenation unit 104 may include a dehydrogenation catalyst comprising chromia/alumina, Pt/alumina, or combinations thereof.

According to embodiments of the invention, an outlet of dehydrogenation unit 104 may be in fluid communication with an inlet of etherification unit 105 such that dehydrogenation unit effluent stream 15 is flowed from dehydrogenation unit 104 to etherification unit 105. In embodiments of the invention, etherification unit 105 is configured to react isobutene of dehydrogenation unit effluent stream 15 with an alkanol under reaction conditions sufficient to produce product stream 16 comprising an alkyl tert-butyl ether and recycle stream 17 comprising unreacted isobutane. In embodiments of the invention, the alkyl tert-butyl ether includes MTBE and/or ethyl tert-butyl ether (ETBE). Etherification unit 105 may comprise an MTBE and/or ETBE synthesis reactor, and an effluent separator configured to separate an effluent from the MTBE and/or ETBE synthesis reactor to form product stream 16 comprising MTBE and/or ETBE and recycle stream 17 comprising isobutane. The MTBE and/or ETBE synthesis reactor can include a catalyst for catalyzing MTBE and/or ETBE synthesis reaction including cation exchange resin, sulfonated styrene divinyl benzene, polystyrene polymer mounted cation exchange resin, or combinations thereof. In embodiments of the invention, an outlet of etherification unit 105 is in fluid communication with an inlet of dehydrogenation unit 104 such that recycle stream 17 is flowed from etherification unit 105 back to dehydrogenation unit 104.

Figure 1B:
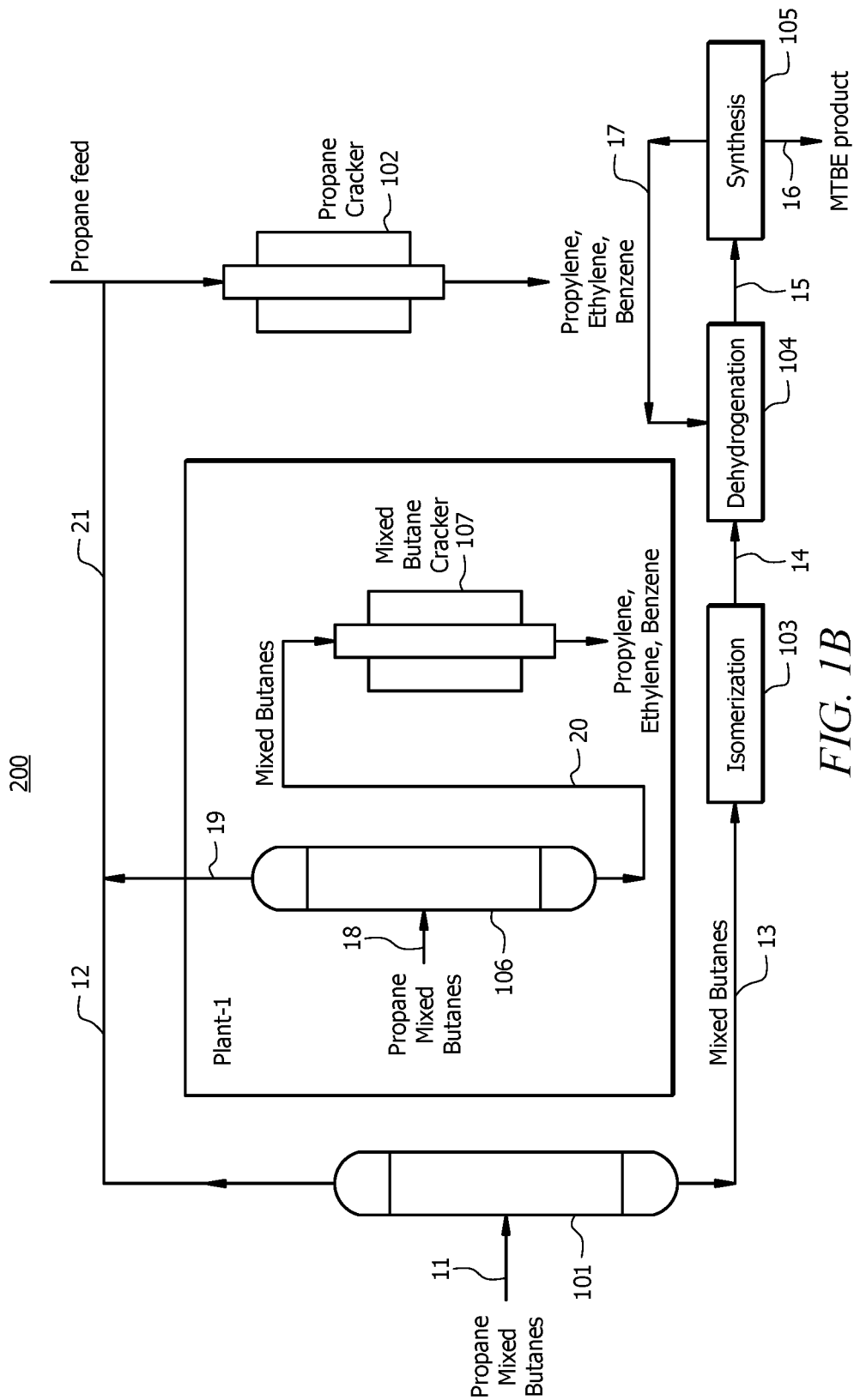

As shown in FIG. 1B, system 200 includes all the streams and units of system 100. According to embodiments of the invention, system 200 further includes second separation unit 106 configured to receive and separate second feed stream 18 comprising $C_3$ and $C_4$ hydrocarbons to form second $C_3$ stream 19 and second $C_4$ stream 20. In embodiments of the invention, second feed stream 18 further comprises methane and $C_2$ hydrocarbons. Second $C_3$ stream 19 may comprise primarily propane. Second $C_4$ stream 20 may comprise primarily n-butane and isobutane. Second feed stream 18, in embodiments of the invention, may include liquefied petroleum gas. Second separation unit 106 may include a depropanizer column.

According to embodiments of the invention, a top outlet of second separation unit 106 may be in fluid communication with an inlet of cracking unit 102 such that second $C_3$ stream 19 flows from second separation unit 106 to cracking unit 102. In embodiments of the invention, second $C_3$ stream 19 may be combined with first $C_3$ stream 12 to form combined $C_3$ stream 21. Combined $C_3$ stream 21 may be flowed to cracking unit 102. According to embodiments of the invention, a bottom outlet of second separation unit 106 may be in fluid communication with an inlet of mixed butane cracking unit 107 such that second $C_4$ stream 20 flows from second separation unit 106 to mixed butane cracking unit 107. Mixed butane cracking unit 107 may be configured to crack n-butane and/or isobutane of second $C_4$ stream 20 to produce light olefins and/or aromatics. The light olefins may include ethylene and propylene. The aromatics may include benzene. In embodiments of the invention, second separation unit 106 and mixed butane cracking unit 107 may be in a separate chemical production plant from system 100.

Figure 1C:
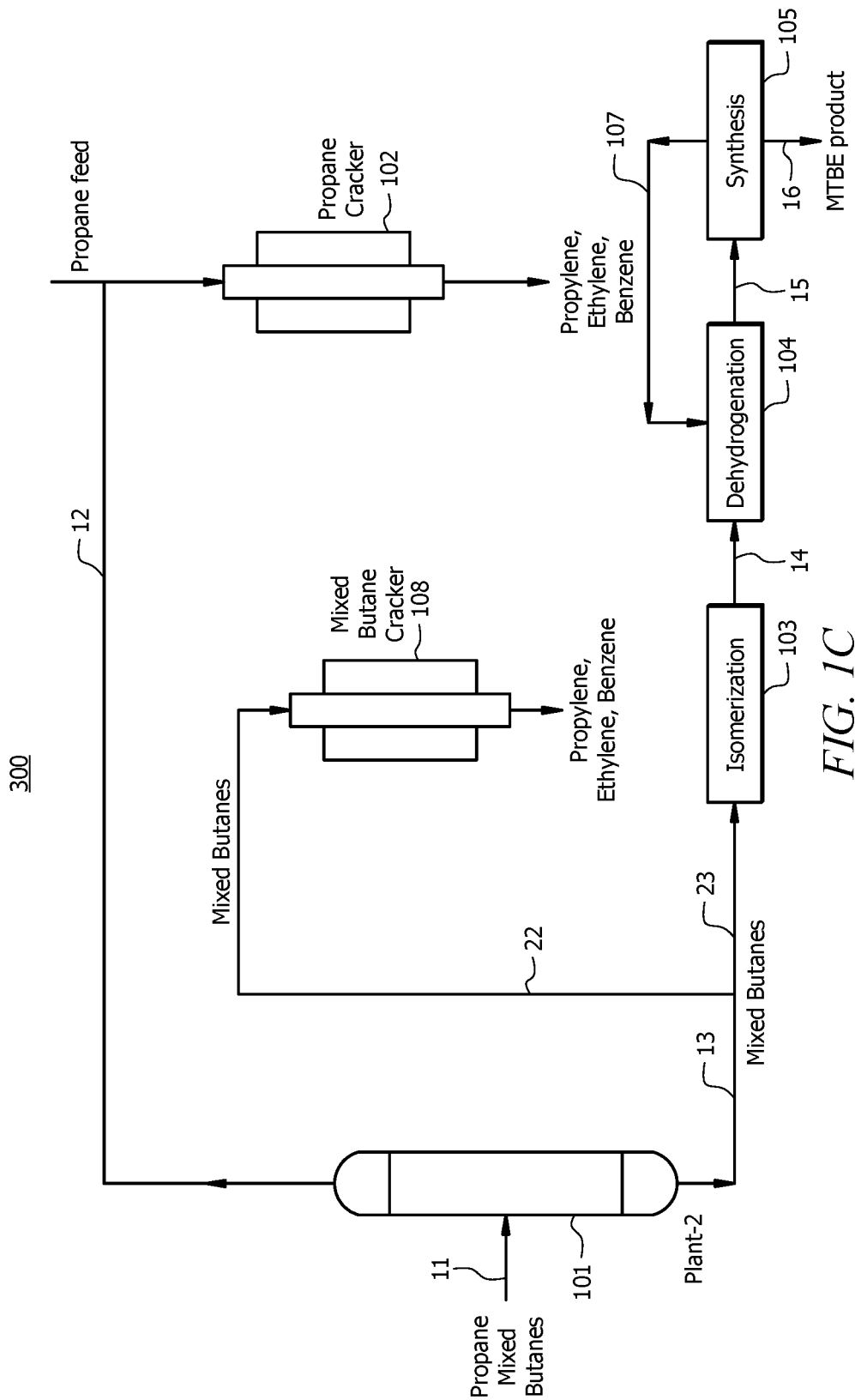

As shown in FIG. 1C, system 300 includes all the streams and units of system 100. According to embodiments of the invention, system 300 further includes second mixed butane cracking unit 108. An outlet of first separation unit 101 may be in fluid communication with second mixed butane cracking unit 108 such that at least a portion of first $C_4$ stream 13, which forms cracker feed stream 22, flows from first separation unit 101 to second mixed butane cracking unit 108. Second mixed butane cracking unit 108 may be configured to crack n-butane and/or isobutane of cracker feed stream 22 to produce light olefins and/or aromatics. In embodiments of the invention, the light olefins can include ethylene and/or propylene. The aromatics may include benzene.

B. Method of Processing $C_3$ and $C_4$ Hydrocarbon Mixture

Figure 2:
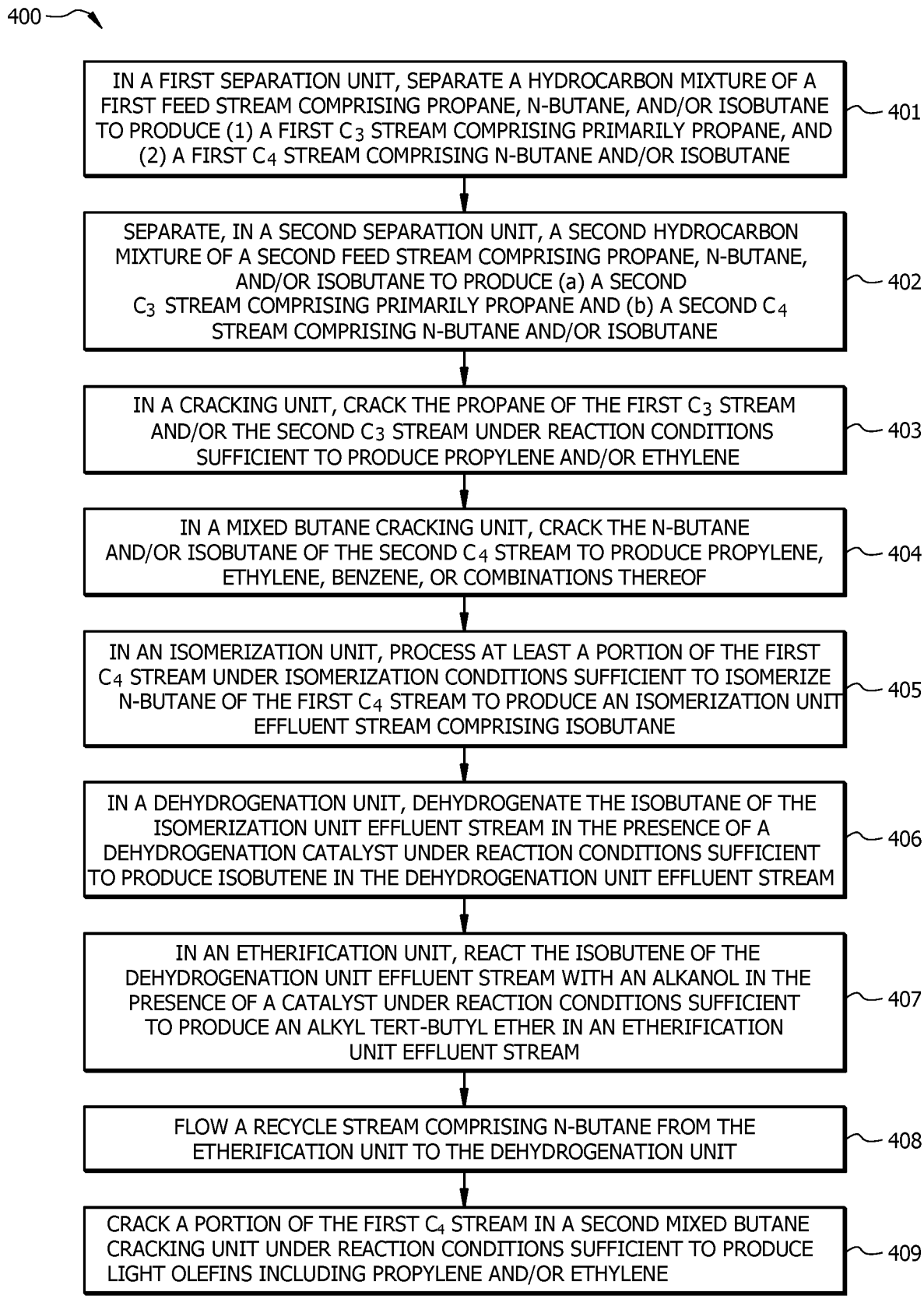
FIG. 2 shows a schematic flowchart of a method for producing MTBE, according to embodiments of the invention.

Methods of processing a $C_3$ and $C_4$ hydrocarbon mixture have been discovered. As shown in FIG. 2, embodiments of the invention include a method 400 for processing a $C_3$ and $C_4$ hydrocarbon mixture for producing an alkyl tert-butyl ether with improved efficiency and reduced energy consumption compared to conventional methods. Method 400 may be implemented by systems 100, 200 and/or 300, as shown in FIGS. 1A-1C and described above.

According to embodiments of the invention, as shown in in block 401, method 400 includes, in first separation unit 101, separating a hydrocarbon mixture of first feed stream 11 comprising propane, n-butane, and/or isobutane to produce (1) first $C_3$ stream 12 comprising primarily propane, and (2) first $C_4$ stream 13 comprising n-butane and/or isobutane. First feed stream 11 may include 20 to 30 wt. % isobutane, 60 to 80 wt. % n-butane, and 0 to 7 wt. % propane. First feed stream 11 may further include methane and/or $C_2$ hydrocarbons, and first $C_3$ stream 12 may further include methane and/or $C_2$ hydrocarbons from first feed stream 11. In embodiments of the invention, at block 401, first separation unit 101 is operated at an overhead condensing temperature range of 30 to 40° C., and a bottom temperature range of 60 to 120° C. First separation unit 101, at block 401, may be operated at an operating pressure of 15 to 18 bar and all ranges and values there between including ranges of 15 to 16 bar, 16 to 17 bar, and 17 to 18 bar. In embodiments of the invention, first $C_3$ stream 12 includes 95 to 99.9 wt. % propane. First $C_4$ stream 13 may include 60 to 75 wt. % n-butane and 20 to 40 wt. % isobutane.

According to embodiments of the invention, as shown in block 402, method 400 includes separating, in second separation unit 106, a second hydrocarbon mixture of second feed stream 18 comprising propane, n-butane, and/or isobutane to produce (a) second $C_3$ stream 19 comprising primarily propane and (b) second $C_4$ stream 20 comprising n-butane and/or isobutane. In embodiments of the invention, second feed stream 18 comprises 20 to 30 wt. % isobutane, 60 to 80 wt. % n-butane, and 0 to 7 wt. % propane. Second feed stream 18 may further include methane and/or $C_2$ hydrocarbons. Second feed stream 18, according to embodiments of the invention, includes liquefied petroleum gas. In embodiments of the invention, second separation unit 106 may include a distillation column. At block 402, the distillation column may be operated at an overhead condensing range of 30 to 40° C., a bottom temperature range of 60 to 120° C., and an operating pressure of 15 to 18 bar. Second $C_3$ stream 19 may comprise 95 to 99.9 wt. % propane. Second $C_4$ stream 20 may comprise 60 to 80 wt. % n-butane and 20 to 30 wt. % isobutane. In embodiments of the invention, second $C_3$ stream 19 may be combined with first $C_3$ stream 12 to form combined $C_3$ stream 21.

According to embodiments of the invention, as shown in block 403, method 400 includes, in cracking unit 102, cracking the propane of first $C_3$ stream 12 and/or second $C_3$ stream 19 under reaction conditions sufficient to produce propylene and/or ethylene. Cracking at block 403 may further produce benzene. In embodiments of the invention, cracking unit 102 includes a steam cracker. The steam cracker may be operated at an operating temperature of 750 to 890° C. and a residence time of 0.1 to 0.5 seconds.

According to embodiments of the invention, as shown in block 404, method 400 includes, in mixed butane cracking unit 107, cracking the n-butane and/or isobutane of second $C_4$ stream 20 to produce propylene, ethylene, benzene, or combinations thereof. Mixed butane cracking unit 107 may include a steam cracker. In embodiments of the invention, cracking at block 404 may be performed at a cracking temperature of 750 to 890° C. and a residence time of 0.1 to 0.5 seconds.

According to embodiments of the invention, as shown in block 405, method 400 includes, in isomerization unit 103, processing at least a portion of first $C_4$ stream 13 under isomerization conditions sufficient to isomerize n-butane of first $C_4$ stream 13 to produce isomerization unit effluent stream 14 comprising isobutane. In embodiments of the invention, isomerization unit effluent stream 14 may comprise 95 to 99.5 wt. % isobutane and all ranges and values there between including ranges of 95 to 95.5 wt. %, 95.5 to 96 wt. %, 96 to 96.5 wt. %, 96.5 to 97 wt. %, 97 to 97.5 wt. %, 97.5 to 98 wt. %, 98 to 98.5 wt. %, 98.5 to 99 wt. %, and 99 to 99.5 wt. %. At block 405, reaction conditions in isomerization unit 103 can include a reaction temperature of 125 to 175° C. and all ranges and values there between. The reaction conditions in isomerization unit 103 at block 405 may further include a reaction pressure of 20 to 30 bar and all ranges and values there between. The reaction conditions in isomerization unit 101 at block 405 may further still include a weight hourly space velocity in a range of 4 to 6 $hr^{-1}$ and all ranges and values there between.

According to embodiments of the invention, as shown in block 406, method 400 includes, in dehydrogenation unit 104, dehydrogenating the isobutane of isomerization unit effluent stream 14 in the presence of a dehydrogenation catalyst under reaction conditions sufficient to produce isobutene in dehydrogenation unit effluent stream 15. In embodiments of the invention, the reaction conditions at block 406 include a reaction temperature of 520 to 640° C., a reaction pressure of 0.36 to 1.2 bar, and/or a weight hourly space velocity in a range of 0.2 to 1.2 $hr^{-1}$. Dehydrogenation unit effluent stream 15 may include 35 to 65 wt. % isobutene and all ranges and values there between including ranges of 35 to 40 wt. %, 40 to 45 wt. %, 45 to 50 wt. %, 50 to 55 wt. %, 55 to 60 wt. %, and 60 to 65 wt. %.

According to embodiments of the invention, as shown in block 407, method 400 includes, in etherification unit 105, reacting the isobutene of dehydrogenation unit effluent stream 15 with an alkanol in the presence of a catalyst under reaction conditions sufficient to produce alkyl tert-butyl ether in an etherification unit effluent stream. In embodiments of the invention, non-limiting examples of the alkanol include methanol and ethanol. Non-limiting examples of the alkyl tert-butyl ether may include methyl tert-butyl ether (MTBE) and ethyl tert-butyl ether (ETBE). The etherification catalyst may include cation exchange resin, polystyrene divinyl benzene mounted ion exchange resin, polymeric support mounted ion exchange resin, or combinations thereof. The reaction conditions in etherification unit 105, at block 407, may include an etherification temperature of 40 to 55° C., an etherification pressure of 5 to 8 bar, and a liquid hourly space velocity of 2 to 4 $hr^{-1}$. In embodiments of the invention, at block 407, the etherification unit effluent stream is further separated to produce product stream 16 comprising primarily the alkyl tert-butyl ether and recycle stream 17 comprising primarily isobutane. In embodiments of the invention, the alkyl tert-butyl ether is MTBE and product stream 16 comprises 98 to 99.5 wt. % MTBE.

According to embodiments of the invention, as shown in block 408, method 400 includes flowing recycle stream 17 from etherification unit 105 to dehydrogenation unit 104. In embodiments of the invention, as shown in block 409, method 400 includes cracking a portion of first $C_4$ stream 13 in second mixed butane cracking unit 108 under reaction conditions sufficient to produce light olefins including propylene and/or ethylene. Cracking at block 409 may further produce benzene. In embodiments of the invention, cracking at block 409 is conducted at a cracking temperature of 750 to 890° C. and a residence time of 0.1 to 0.5 seconds.

Although embodiments of the present invention have been described with reference to blocks of FIG. 2, it should be appreciated that operation of the present invention is not limited to the particular blocks and/or the particular order of the blocks illustrated in FIG. 2. Accordingly, embodiments of the invention may provide functionality as described herein using various blocks in a sequence different than that of FIG. 2.

The systems and processes described herein can also include various equipment that is not shown and is known to one of skill in the art of chemical processing. For example, some controllers, piping, computers, valves, pumps, heaters, thermocouples, pressure indicators, mixers, heat exchangers, and the like may not be shown.

As part of the disclosure of the present invention, specific examples are included below. The examples are for illustrative purposes only and are not intended to limit the invention. Those of ordinary skill in the art will readily recognize parameters that can be changed or modified to yield essentially the same results.

Example 1

Simulation on Propane Production

The feed in the examples below was obtained by statistical analysis of two years of actual operating information from a liquefied petroleum gas (LPG) feed unit (for all results shown in Tables 1 to 3). The bottoms and distillate compositions were obtained by simulation of the column suited to this service. Table 1 and Table 3 have variation in propane product specification. The results in Table 3 is matched to commercial cracker feed purity propane. Table 2 shows the maximum propane in LPG feed.

TABLE 1

Results obtained with low propane feed

| | Feed wt % | Bottoms wt % | Distillate wt % |
|---|---|---|---|
| PROPANE | 2.34% | 0.00% | 99.90% |
| ISOBUTANE | 24.45% | 25.03% | 0.10% |
| BUTANE | 72.80% | 74.55% | 0.00% |
| PENTANE | 0.41% | 0.42% | 0.00% |
| Total | 100.00% | 100.00% | 100.00% |
| MT/hr | 145.99 | 142.57 | 3.42 |

TABLE 2

Results obtained with maximum propane feed

| | Feed wt % | Bottoms wt % | Distillate wt % |
|---|---|---|---|
| PROPANE | 6.50% | 0.00% | 99.96% |
| ISOBUTANE | 23.28% | 24.89% | 0.04% |
| BUTANE | 69.32% | 74.14% | 0.00% |
| PENTANE | 0.90% | 0.96% | 0.00% |
| Total | 100.00% | 100.00% | 100.00% |
| MT/hr | 145.99 | 136.50 | 9.49 |

TABLE 3

Results obtained with Commercial purity propane specification

| | Feed wt % | Bottoms wt % | Distillate wt % |
|---|---|---|---|
| PROPANE | 2.34% | 0.12% | 95.00% |
| ISOBUTANE | 24.45% | 24.92% | 5.00% |
| BUTANE | 72.80% | 74.54% | 0.00% |
| PENTANE | 0.41% | 0.42% | 0.00% |
| Total | 100.00% | 100.00% | 100.00% |
| MT/hr | 330.00 | 322.28 | 7.72 |

In the context of the present invention, at least the following 15 embodiments are described. Embodiment 1 is a method of processing a hydrocarbon mixture. The method includes separating a hydrocarbon mixture containing propane, n-butane, and/or isobutane to produce (1) a $C_3$ stream containing primarily propane, and (2) a $C_4$ stream containing n-butane and/or isobutane. The method further includes cracking the propane of the $C_3$ stream under reaction conditions sufficient to produce propylene and/or ethylene. The method still further includes processing at least a portion of the $C_4$ stream under isomerization conditions sufficient to isomerize n-butane of the $C_4$ stream to produce an isomerization unit effluent containing isobutane. Embodiment 2 is the method of embodiment 1, further including dehydrogenating the isobutane of the isomerization unit effluent in a dehydrogenation unit to produce isobutene in a dehydrogenation unit effluent. The method further includes reacting, in an etherification unit, the isobutene of the dehydrogenation unit effluent with an alkanol in the presence of a catalyst under reaction conditions sufficient to produce an alkyl tert-butyl ether in an etherification unit effluent. Embodiment 3 is the method of embodiment 2, wherein the dehydrogenation unit effluent contains 35 to 60 wt. % isobutene. Embodiment 4 is the method of either of embodiments 2 or 3, wherein the etherification unit effluent contains at least some isobutane, the method further including recycling at least some isobutane from the etherification unit effluent to the dehydrogenation unit. Embodiment 5 is the method of any of embodiments 2 to 4, wherein the dehydrogenation unit includes a dehydrogenation catalyst containing chromia/alumina, Pt/alumina, or combinations thereof. Embodiment 6 is the method of any of embodiments 2 to 5, wherein the alkanol includes methanol and/or ethanol. Embodiment 7 is the method of any of embodiments 2 to 6, wherein the alkyl tert-butyl ether includes methyl tert-butyl ether and/or ethyl tert-butyl ether. Embodiment 8 is the method of any of embodiments 1 to 7, further including cracking at least a portion of the $C_4$ stream in a mixed butane cracker to produce propylene ethylene, and/or benzene. Embodiment 9 is the method of any of embodiments 1 to 8, wherein the $C_4$ stream contains 60 to 75 wt. % n-butane and 20 to 40 wt. % isobutane. Embodiment 10 is the method of any of embodiments 1 to 9, wherein the $C_3$ stream contains 95 to 99.9 wt. % propane. Embodiment 11 is the method of any of embodiments 1 to 10, wherein the isomerization unit effluent contains 95 to 99.9 wt. % isobutane. Embodiment 12 is the method of any of embodiments 1 to 11, wherein the hydrocarbon mixture includes liquefied petroleum gas. Embodiment 13 is the method of any of embodiments 1 to 12, wherein the cracking of propane is performed in a steam cracker at a temperature of 750 to 900° C. and a steam cracker residence time of 0.1 to 0.5 s. Embodiment 14 is the method of any of embodiments 1 to 13, wherein the isomerization unit contains an isomerization catalyst containing $Pt/AlCl_3/Al_2O_3$, $Pt/AlCl_3$/zeolite, $Pt/SO_4^{2-}$—$ZrO_2$, $SO_4^{2-}$/$ZrO_2$—$Al_2O_3$, or combinations thereof.

Embodiment 15 is a method of processing hydrocarbon mixtures. The method includes separating a first hydrocarbon mixture containing propane, n-butane, and/or isobutane to produce (1) a first $C_3$ stream containing primarily propane, and (2) a first $C_4$ stream containing n-butane and/or isobutane. The method further includes separating a second hydrocarbon mixture containing propane, n-butane, and/or isobutane to produce (a) a second $C_3$ stream containing primarily propane, and (b) a second $C_4$ stream containing n-butane and/or isobutane. The method still further includes cracking the propane of the first $C_3$ stream and the second $C_3$ stream under reaction conditions sufficient to produce propylene and cracking the n-butane and/or isobutane of the second $C_4$ stream to produce propylene, ethylene and/or benzene. The method also includes processing at least a portion of the first $C_4$ stream under isomerization conditions sufficient to isomerize n-butane of the first $C_4$ stream to produce an isomerization unit effluent containing isobutane. In addition, the method includes dehydrogenating the isobutane of the isomerization unit effluent in a dehydrogenation unit to produce isobutene in a dehydrogenation unit effluent, and reacting, in an etherification unit, the isobutene of the dehydrogenation unit effluent with an alkynol in the presence of a catalyst under reaction conditions sufficient to produce an alkyl tert-butyl ether in an etherification unit effluent.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of processing a hydrocarbon mixture, the method comprising:
    separating a hydrocarbon mixture comprising propane, n-butane, and/or isobutane to produce (1) a $C_3$ stream comprising primarily propane, and (2) a $C_4$ stream comprising n-butane and/or isobutane;
    steam cracking the propane of the $C_3$ stream under reaction conditions sufficient to produce at least one olefin selected from propylene or ethylene;
    processing at least a portion of the $C_4$ stream under isomerization conditions sufficient to isomerize n-butane of the $C_4$ stream to produce an isomerization unit effluent comprising isobutane; and
    cracking at least a portion of the C4 stream in a mixed butane cracker to produce propylene, ethylene, and/or benzene;
    wherein the dehydrogenation unit effluent comprises 35 to 60 wt. % isobutene.

2. The method of claim 1, further comprising: dehydrogenating the isobutane of the isomerization unit effluent in a dehydrogenation unit to produce isobutene in a dehydrogenation unit effluent; and
    reacting, in an etherification unit, the isobutene of the dehydrogenation unit effluent with an alkanol in the presence of a catalyst under reaction conditions sufficient to produce an alkyl tert-butyl ether in an etherification unit effluent.

3. The method of claim 2, wherein the dehydrogenation unit effluent comprises 60 wt. % isobutene.

4. The method of claim 2, wherein the etherification unit effluent comprises at least some isobutane, the method further comprising: recycling at least some isobutane from the etherification unit effluent to the dehydrogenation unit.

5. The method of claim 2, wherein the dehydrogenation unit comprises a dehydrogenation catalyst comprising chromia/alumina, Pt/alumina, or combinations thereof.

6. The method of claim 2, wherein the alkanol comprises methanol and/or ethanol.

7. The method of claim 2, wherein the alkyl tert-butyl ether comprises methyl tert-butyl ether and/or ethyl tert-butyl ether.

8. The method of claim 2, wherein the alkyl tert-butyl ether comprises methyl tert-butyl ether.

9. The method of claim 1, wherein the $C_4$ stream comprises 60 to 75 wt. % n-butane and 20 to 40 wt. % isobutane.

10. The method of claim 1, wherein the $C_3$ stream comprises 95 to 99.9 wt. % propane.

11. The method of claim 1, wherein the isomerization unit effluent comprises 95 to 99.9 wt. % isobutane.

12. The method of claim 1, wherein the hydrocarbon mixture includes liquefied petroleum gas.

13. The method of claim 1, wherein the cracking of propane is performed in a steam cracker at a temperature of 750 to 900° C. and a steam cracker residence time of 0.1 to 0.5 s.

14. The method of claim 1, wherein the isomerization unit comprises an isomerization catalyst comprising Pt/All/$Al_2O_3$, Pt/$AlCl_3$/zeolite, Pt/$SO_4^{2-}$—$ZrO_2$, $SO_4^{2-}$/$ZrO_2$—$Al_2O_3$, or combinations thereof.

15. A method of processing hydrocarbon mixtures, the method comprising:
    separating a first hydrocarbon mixture comprising propane, n-butane, and/or isobutane to produce (1) a first $C_3$ stream comprising primarily propane, and (2) a first $C_4$ stream comprising n-butane and/or isobutane;
    separating a second hydrocarbon mixture comprising propane, n-butane, and/or isobutane to produce (a) a second $C_3$ stream comprising primarily propane, and (b) a second $C_4$ stream comprising n-butane and/or isobutane;
    steam cracking the propane of the first $C_3$ stream and the second $C_3$ stream under reaction conditions sufficient to produce propylene;
    cracking the n-butane and/or isobutane of the second $C_4$ stream to produce propylene, ethylene and/or benzene;
    processing at least a portion of the first $C_4$ stream under isomerization conditions sufficient to isomerize n-butane of the first $C_4$ stream to produce an isomerization unit effluent comprising isobutane;
    dehydrogenating the isobutane of the isomerization unit effluent in a dehydrogenation unit to produce isobutene in a dehydrogenation unit effluent; and
    reacting, in an etherification unit, the isobutene of the dehydrogenation unit effluent with an alkynol in the presence of a catalyst under reaction conditions sufficient to produce an alkyl tert-butyl ether in an etherification unit effluent.

16. The method of claim 2, wherein the $C_3$ stream comprises 95 to 99.9 wt. % propane.

17. The method of claim 2, wherein the isomerization unit effluent comprises 95 to 99.9 wt. % isobutane.

18. The method of claim 2, wherein the hydrocarbon mixture includes liquefied petroleum gas.

19. The method of claim 2, wherein the cracking of propane is performed in a steam cracker at a temperature of 750 to 900° C. and a steam cracker residence time of 0.1 to 0.5 s.

20. The method of claim 2, wherein the isomerization unit comprises an isomerization catalyst comprising Pt/$AlCl_3$/$Al_2O_3$, Pt/$AlCl_3$/zeolite, Pt/$SO_4^{2-}$—$ZrO_2$, $SO_4^{2-}$/$ZrO_2$—$Al_2O_3$, or combinations thereof.

* * * * *